United States Patent [19]

Loosmore et al.

[11] Patent Number: 5,439,810
[45] Date of Patent: Aug. 8, 1995

[54] MANIPULATION OF GENE COPY NUMBER IN BORDETELLA

[75] Inventors: Sheena Loosmore, Aurora; Gavin Zealey, Thornhill; Reza Yacoob, Mississauga; Michel Klein, Willowdale, all of Canada

[73] Assignee: Connaught Laboratories Limited, Willowdale, Canada

[21] Appl. No.: 911,291

[22] Filed: Jul. 9, 1992

[30] Foreign Application Priority Data

Jul. 16, 1991 [GB] United Kingdom .................. 9115332

[51] Int. Cl.$^6$ ...................... A61K 35/14; A61K 39/10; C12N 1/21; C12N 15/09
[52] U.S. Cl. ................................ 435/69.3; 424/234.1; 424/235.1; 424/240.1; 435/69.1; 435/172.3; 435/243; 435/252.3; 435/320.1; 536/23.1; 536/23.2; 536/23.7
[58] Field of Search ............. 424/88, 92, 234.1, 235.1, 424/240.1; 435/69.1, 172.3, 243, 69.3, 320.1, 252.3; 935/38; 536/27, 23.1, 23.2, 23.7

[56] References Cited

U.S. PATENT DOCUMENTS 4,997,915  3/1991  Tan et al. ............................ 530/396
5,085,862  2/1992  Klein et al. ............................ 424/92

FOREIGN PATENT DOCUMENTS 0322115  6/1989  European Pat. Off. .

OTHER PUBLICATIONS

Loosmore et al., Infect. Immun. 58, 3653 (1990).
Lee et al., (1989, Infect. Immun. 57: 1413–1418).
Nicosia et al., Proc. Natl. Acad. Sci. USA 83, 4631 (1986).
Loosmore et al., Nucl. Acids Res. 17, 8365 (1989).
Relman et al., Proc. Natl. Acad. Sci. USA 86, 2637 (1989).
Charles et al., Proc. Natl. Acad. Sci. USA 86, 3554 (1989).
Glaser et al., Molec. Microbiol. 2, 19 (1988).
Pizza et al., Science 246, 497 (1989).
Zealey et al., Bio/Technology 8, 1025 (1990).
Sambrook et al. (Molecular cloning: a laboratory manual/second edition. Cold Spring Harbor Laboratory, Cold Spring Harbor, N.Y. (1989).
Ish-Horowicz and Burke (Nucl. Acids Res. 9, 2989 (1988).
Yacoob and Zealey (Nucl. Acids Res. 16, 1639 (1988).
Imaizumi et al., Infect. Immun. 41, 1138 (1983).

*Primary Examiner*—Christine M. Nucker
*Assistant Examiner*—Michael Tuscan
*Attorney, Agent, or Firm*—Sim & McBurney

[57] ABSTRACT

Protein expression levels from Bordetella strains, particularly *Bordetella pertussis*, are altered by genetic modification to a natural Bordetella strain whereby one or more of the natural genes, particularly including the TOX, FHA, CYA and PRN genes, is deleted from the genome of the natural strain and one or more of the natural genes or a genetic mutation thereof, particularly a genetically-detoxified TOX* gene, or a hybrid gene, is inserted into the genome of the natural strain to provide at least two copies of one or more of the natural genes or genetic mutation thereof or hybrid gene, singly or in tandem. The altered genotype Bordetella strain is useful in producing whole-cell or defined component vaccines against Bordetella, particularly whooping cough, which may be employed in combination with other vaccines.

20 Claims, 13 Drawing Sheets

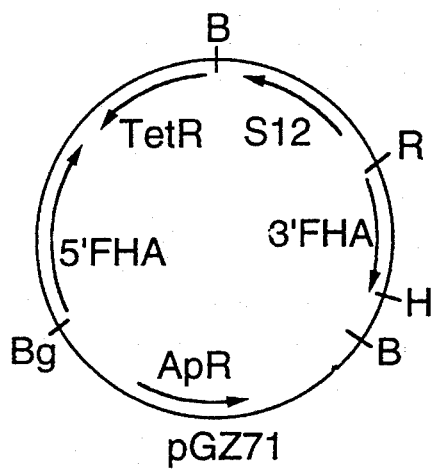
pGZ71
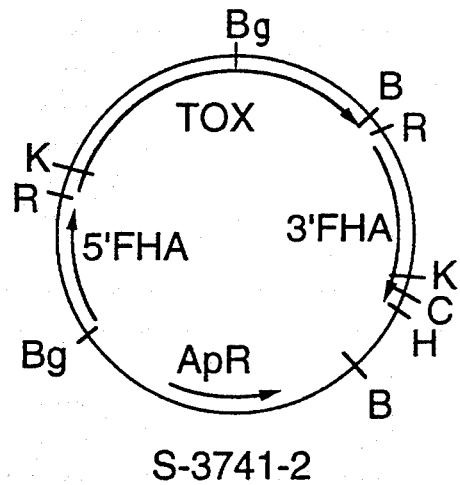
S-3741-2
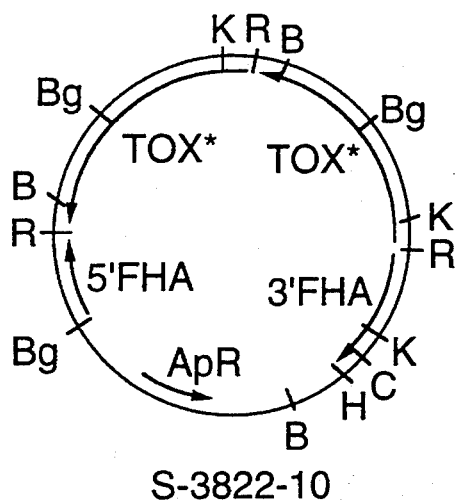
S-3822-10
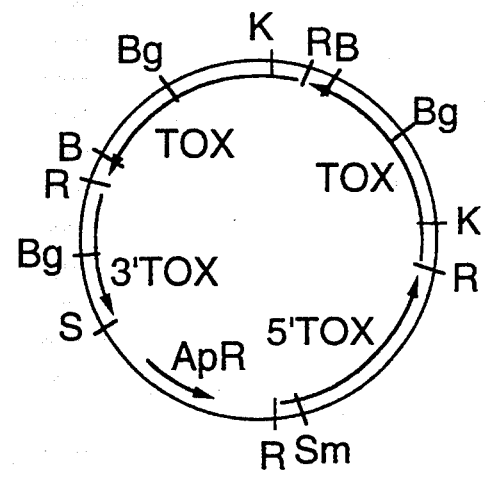
S-4000-5 (Lys9Gly129)
S-3980-9 (wild-type)
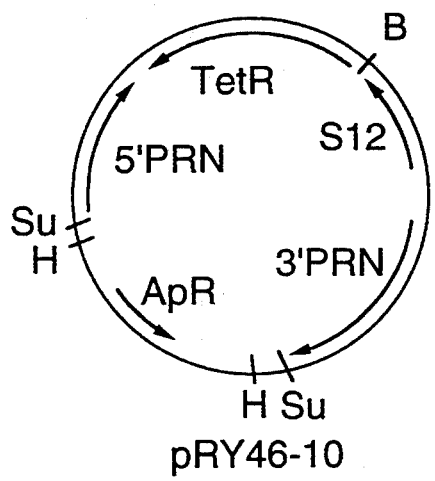
pRY46-10
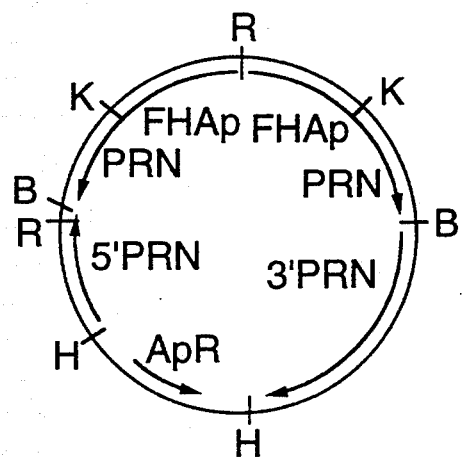
S-4258-7
FIG.1A.

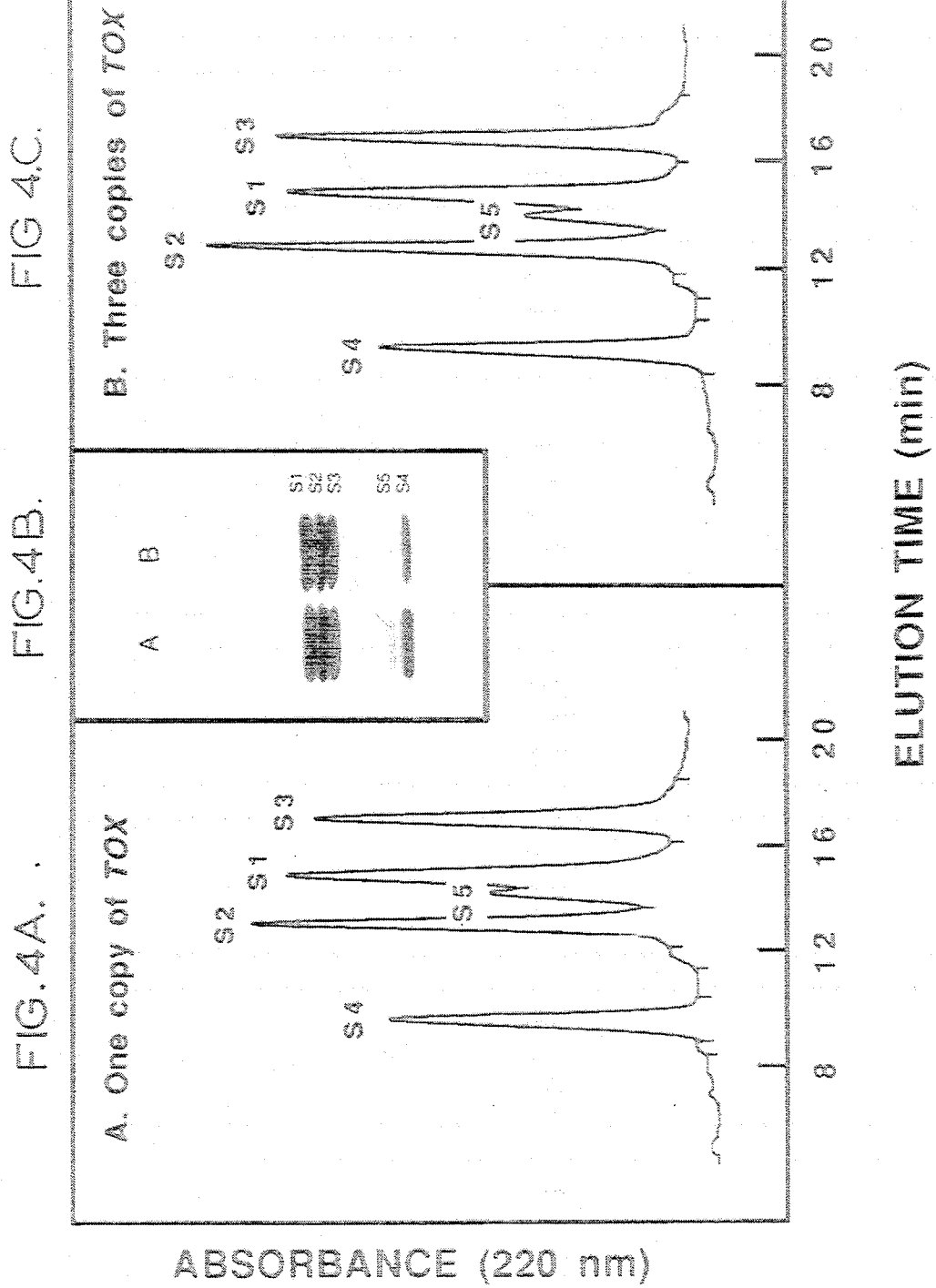

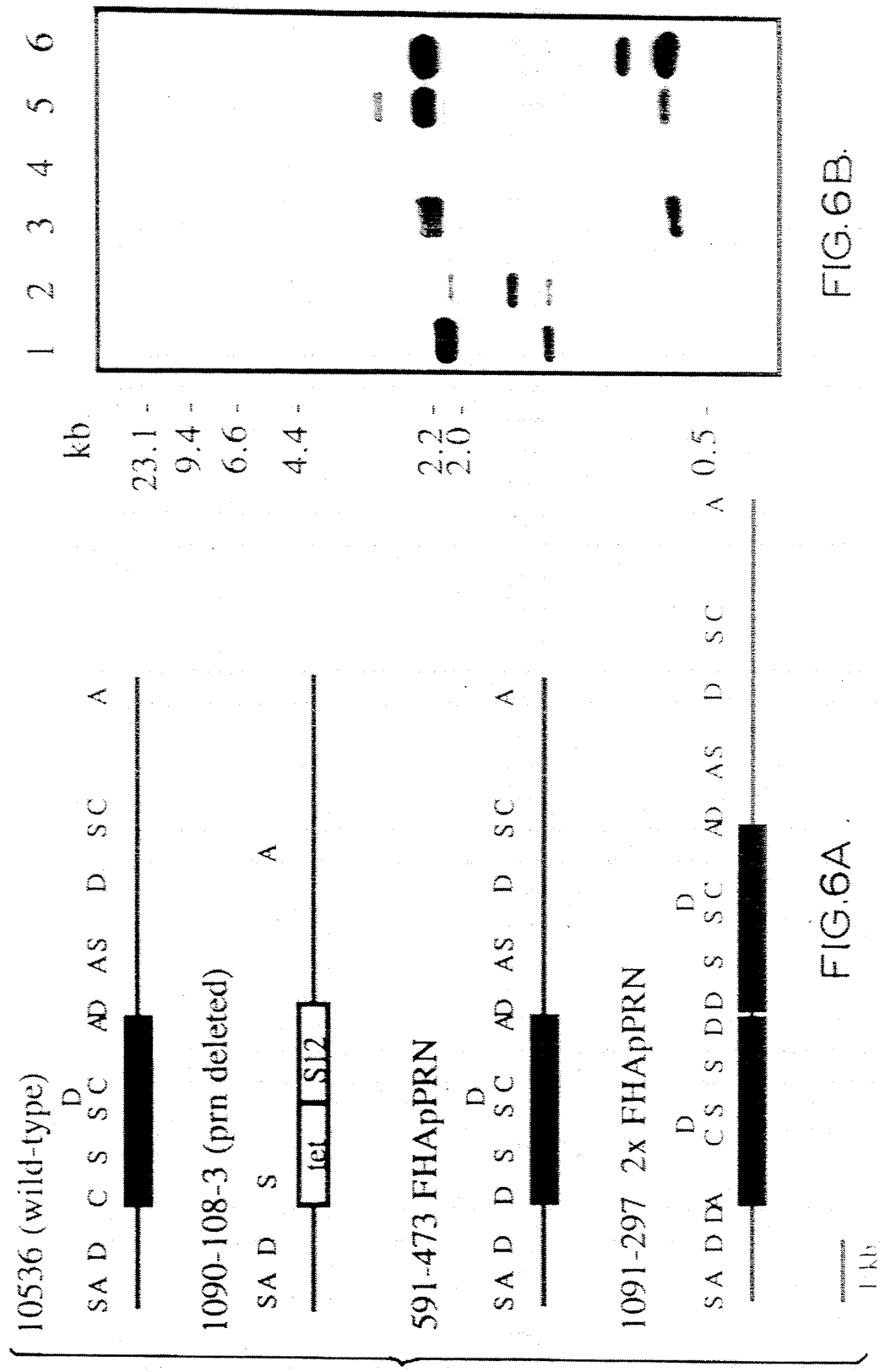

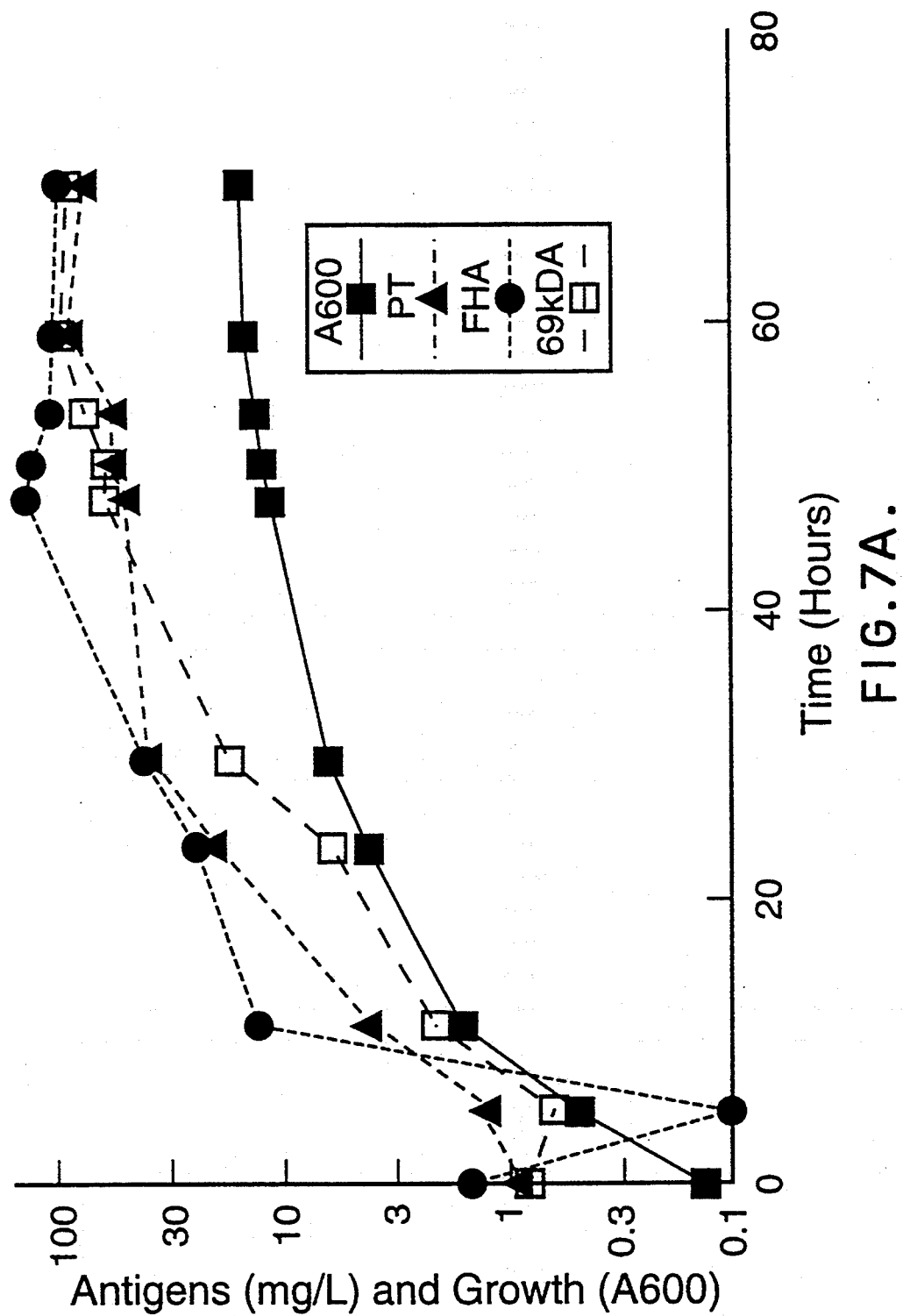

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:1:

AATGAACATG TCTCTGTCAC GCATTGTCAA    30

(2) INFORMATION FOR SEQ ID NO:2:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:2:

TTCCACGCGG GCTACCGGTA CAGCTGGTAA    30

MANIPULATION OF GENE COPY NUMBER IN BORDETELLA

FIELD OF INVENTION

The present invention relates to a novel approach to alter gene expression in Bordetella species by manipulation of gene copy number.

BACKGROUND OF THE INVENTION

Whooping cough in humans is caused by members of the Bordetella species, especially *B. pertussis*. Following disease or vaccination, antibodies are elicited against several bacterial proteins, especially pertussis toxin (PT), filamentous haemagglutinin (FHA), the 69kDa outer membrane protein (69kD or pertactin) and the fimbrial agglutinogens. PT is a major protective antigen and is also associated with virulence. These antigens have been proposed to formulate single or multi-component pertussis vaccines and, as such, their efficient production and purification are essential.

During fermentation of *B. pertussis*, it has been found that FHA is secreted at 7 and 10 times the molar levels of 69kD or PT, respectively. Therefore, PT and pertactin are limiting antigens in the production of a component vaccine. Furthermore, the relative overproduction of FHA makes the purification of other antigens expressed at lower levels more difficult. This is especially true for PT, which may be initially co-purified with FHA in some purification protocols. It is also of concern that active PT may contaminate the FHA preparation, which then needs to be chemically detoxified to inactivate the residual native toxin. In the case of genetically detoxified pertussis toxin (described in published EPO patent application No. 0322115 and corresponding U.S. Pat. No. 5,085,862, assigned to the assignee hereof and the disclosure of which is incorporated herein by reference; Loosmore et al., Infect. Immun. 58, 3653 [1990]), this would not be a problem. In either case, it would be advantageous, from a vaccine production viewpoint, to have a *B. pertussis* strain which does not produce FHA and/or one which does not produce PT. For example, an FHA− strain in which the FHA gene has been deleted could be used to produce all other antigens under optimized fermentation and purification conditions. Similarly, a PT− strain would produce FHA with no possibility of contamination by pertussis toxin.

There are *B. pertussis* gene products which are not necessary in a whooping cough vaccine, for example, dermonecrotic toxin (DNT) and possibly adenylate cyclase toxin. The gene loci coding for such products could be considered to be dispensable in a vaccine strain as long as the strain remains viable and produces the other antigens in satisfactory amounts. The deletion of dispensable genes offers the possibility of further genetic manipulation by in situ gene insertion at the loci of gene deletions. For example, the adenylate cyclase gene (CYA) could be deleted and one or more additional copies of one of the candidate vaccine antigen genes inserted at the CYA locus. The additional gene(s) may be introduced through homologous recombination using the flanking sequences of the deleted gene to direct in situ gene insertion. Alternatively, gene copies also may be introduced through random insertion into the chromosome or through the introduction of replicating plasmids. Multiple copies of regulatory genes, such as the vir regulon, Bvg, could also be introduced to modify antigen expression.

Examples of deleted strains could be TOX−, FHA−, PRN−, CYA−, DNT− or any combination of these or other gene deletions. Inserted genes could be any of the TOX, FHA, PRN or any other native, mutated, or hybrid genes and one or more copies could be inserted in tandem or separately. Such genetic manipulations aimed at augmenting a gene copy number with or without deletion of other genes, could lead to substantial enhancement of Bordetella antigen production and/or optimization of antigen purification.

Lee et al (1989, Infect. Immun. 57: 1413–1418) attempted to generate hypertoxigenic strains of *B. pertussis* by expression of the TOX operon from a multicopy replicating plasmid. No increase in PT production was observed, however, and the plasmid was rearranged, the TOX operon deleted or the transconjugants underwent conversion to an avirulent phase.

SUMMARY OF THE INVENTION

In accordance with the present invention, there is provided a novel method to alter gene expression in Bordetella species by the manipulation of gene copy number. One or more genes may be deleted from any Bordetella strain and additional gene copies inserted singly or in tandem to change protein expression levels.

Accordingly, in one aspect of the present invention, there is provided a genetically-modified Bordetella strain, particularly a genetically-modified *Bordetella pertussis* strain, having one or more of the natural genes deleted from the genome and one or more of the natural genes or a genetic mutation thereof or a hybrid gene, inserted into the genome to provide at least two copies of one or more of the natural genes or genetic mutation thereof, or hybrid gene, in the genome, singly or in tandem, to effect alteration of expression levels of proteins encoded by genes present in the genetically-modified strain in comparison to the natural unmodified strains.

The altered expression level of the protein can lead to enhancement of antigen production and optimization of purification of protein.

The altered genotype strains are useful in producing whole-cell or a cellular defined component vaccines against Bordetella, particularly whooping cough, which may be employed in combination with other vaccines.

BRIEF DESCRIPTION OF DRAWINGS

FIGS. 1A–1E

FIG. 1A shows the plasmids used to derive the copy number-altered Bordetella strains described herein. FIGS. 1B, 1C, 1D and 1E describe their construction. pGZ71 contains an *E. coli* S12 and tetracycline resistance gene cassette, as described in U.S. Pat. No. 5,085,862, sandwiched between the FHA gene flanking regions. Plasmid S-3741-2 (ATCC 75031) contains a single copy of TOX sandwiched between the 5' and 3' FHA gene flanking regions. Plasmid S-3822-10 has tandem copies of the mutant TOX operon (TOX*), which encodes the Lys9Gly129 PT analogue, sandwiched between the FHA flanking regions. Plasmids S-3980-9 and S-4000-5 contain tandem copies of TOX or TOX*, respectively, between the 5' and 3' TOX flanking regions. Plasmid pRY46-10 has the S12/Tet$^R$ cassette between the 5' and 3' PRN flanking regions. To increase the production of pertactin, the natural promoter was replaced by the FHA promoter to produce a hybrid gene FHApPRN, as described in published European patent application No. EP 453,216, in the name of the assignee hereof. Plasmid S-4258-7 contains two tandem copies of a hybrid FHApPRN gene.

FIG. 1B illustrates the construction of plasmids pGZ71 and S-3741-2 which is further described in Examples 4 and 5. FIG. 1C illustrates the construction of plasmids S-3822-10 and S-4000-5, further described in Examples 6 and 7. FIG. 1D illustrates the construction of plasmid pRY46-10, which is described in Example 10. FIG. 1E illustrates the construction of plasmid S-4258-7, which is described in Example 11. Restriction sites are B, BamH I; Bal, Bal I; Bg, Bgl II; C, Cla I; H, Hind III; K, Kpn I; Nco, NcoI; R, EcoR I; S, Sal I; Sm, Sma I; and Su, Sau3A I.

FIGS. 4A and 4C shows a comparative analysis by reverse phase HPLC and FIG. 4B shows a comparative analysis by SDS-PAGE of pertussis toxin analogue (S1 Lys9Gly129) purified from culture supernatants of strains 989-56 (TOX*) and 890-393 (3 TOX*), indicating that they are structurally indistinguishable.

FIG. 5A demonstrates the effect of heptakis (2,6-O-dimethyl)β-cyclodextrin on the expression of PT from strain 10536, when grown in a 10 liter fermentor. FIG. 5B demonstrates the effect of β-cyclodextrin on strain 1190-74 (2 TOX) when grown in a 10 liter fermentor.

FIG. 6A shows a schematic representation of the PRN locus and FHApPRN hybrid genes and FIG. 6B shows the Southern blot analysis for B. pertussis strains 10536, 1090-108-3, 591-473, and 1091-297. Lanes 1 and 3, strain 10536, the wild-type parent digested with Dde I and Sal I, respectively; lanes 2 and 5, strain 591-473, containing one copy of the FHApPRN gene, digested with Dde I and Sal I, respectively; lane 4, strain 1090-108-3, the PRN deleted strain containing the S12/Tet$^R$ cassette, digested with Sal I; lane 6, strain 1091-297 containing two copies of the FHApPRN hybrid gene, digested with Sal I. The restricted DNA was probed with a PRN-specific DNA fragment representing the entire PRN gene. Integration of tandem copies of the FHApPRN hybrid gene is shown by the appearance of new PRN-specific hybridization fragments superimposed upon the wild-type pattern. Restriction sites are A, Apa I; C, Cla I; D, Dde I; S, Sal I.

FIGS. 7A-7B

FIG. 7A shows the kinetics of antigen expression from B. pertussis strain 1091-107 when grown in 10 liter fermentors. Strain 1091-107 contains two copies of the wild-type TOX operon integrated at the TOX locus and a single copy of the FHApPRN hybrid gene integrated at the PRN locus. FIG. 7B shows the kinetics of antigen production by B. pertussis strain 1091-359 when grown in 10 liter fermentors. Strain 1091-359 contains two copies of the TOX* operon, encoding the Lys9Gly129 PT analogue, at the TOX locus and a single copy of the FHApPRN hybrid gene integrated at the PRN locus.

DEPOSIT INFORMATION

Figure 1B:
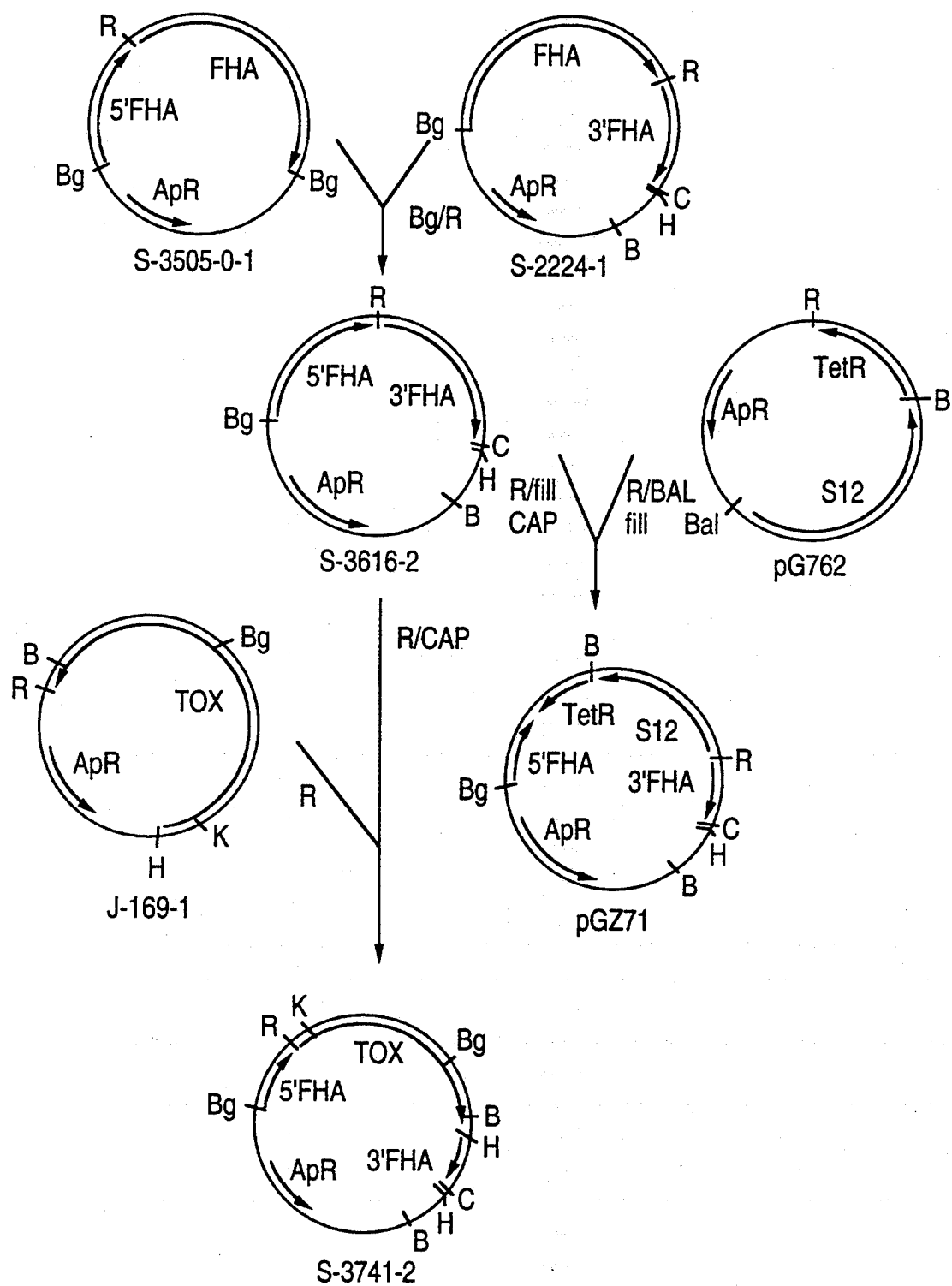

Certain biological materials described herein for the first time have been deposited with the American Type Culture Collection (ATCC) located at Rockville, Md., U.S.A. pursuant to the Budapest Treaty and prior to the filing of this application, identified as follows:

| (a) Bordetella strains: | | |
|---|---|---|
| Strain No. | Accession No. | Deposit Date |
| 191-134 | 55,205 | June 18, 1991 |
| 890-393 | 55,206 | June 18, 1991 |
| 1091-107 | 55,313 | April 2, 1992 |
| 1091-359 | 55,312 | April 2, 1992 |
| 591-473 | 55,321 | April 30, 1992 |
| 1091-27 | 55,462 | August 17, 1993 |

| (b) Plasmid DNA: | | |
|---|---|---|
| Plasmid No. | Accession No. | Deposit Date |
| S-3741-2 | 75031 | June 18, 1991 |
| S-3980-9 | 75033 | June 18, 1991 |

Other deposited biological materials also are referred to and identified herein but have been deposited in connection with other patent and non-patent activities. Cultures of the deposited microorganisms and plasmids will become available to the public on the grant of a patent on this United States patent application. The invention described and claimed herein is not to be limited in scope by the strains of microorganisms and plasmids deposited, since the deposited embodiment is intended only as an illustration of the invention. Any equivalent microorganisms or plasmids that produce equivalent changes in antigen production as described in this application are within the scope of the invention.

GENERAL DESCRIPTION OF INVENTION

The genes for PT (TOX), FHA (FHA), pertactin (PRN), and adenylate cyclase (CYA) have been cloned and sequenced (Nicosia et al., Proc. Natl. Acad. Sci. U.S.A. 83, 4631 [1986]; Loosmore et al., Nucl. Acids Res. 17, 8365 [1989]; Relman et al., Proc. Natl. Acad. Sci. U.S.A. 86, 2637 [1989]; Charles et al., Proc. Natl. Acad. Sci. U.S.A. 86, 3554 [1989]; Glaser et al., Molec. Microbiol. 2, 19 [1988]). Pertussis toxin is a complex protein composed of six polypeptide subunits, encoded by five different structural genes expressed from a single promoter. Its enzymatic and most of its toxic activities are mediated by its subunit S1, while its cell-binding and mitogenic properties are due to the other subunits, which form the B-subunit. Site-directed mutagenesis of selected codons of the S1 and/or B subunit genes leads to detoxification of the holotoxin (EPO 322115, U.S. Pat. No. 5,085,862, and Loosmore et al., Infect. Immun. 58 3653 [1990]).

Deletion of the TOX operon by homologous recombination following electroporetic transformation of DNA into Bordetella pertussis has been described in EPO 322,115 and U.S. Pat. No. 5,085,862. Briefly, the deletion of a gene in a streptomycin-resistant B. pertussis strain using an S12/Tet$^R$ gene cassette, produces a streptomycin sensitive, tetracycline resistant phenotype. Replacement of the selectable cartridge by a further round of recombination results in streptomycin resistance. This procedure allows specific gene replacement in *B. pertussis* without the integration of an antibiotic resistance gene. The S12/Tet$^R$ gene cassette was introduced into the TOX locus by allelic exchange using a 2.9 kb Sau3A I/EcoR I fragment of TOX 5'-flanking region and a 5 kb EcoR I/Sal I fragment of TOX 3'-flanking region. The replacement of the gene cassette by in vitro mutated alleles has been described (EPO 322,115, U.S. Pat. No. 5,085,862; Pizza et al., Science 246, 497 [1989]; Loosmore et al., Infect. Immun. 58, 3653 [1990]; Zealey et al., Bio/Technology 8, 1025 [1990]). Deletion of the FHA and PRN genes was performed using a similar technique. These techniques are used herein to engineer *B. pertussis* strains having duplicated genes at their original and/or new and novel genetic loci (Tables 1A and 1B). These experiments were approved by the Connaught Biosafety Committee and were performed under either level 2 or 3 containment.

*B. pertussis* strain 29-8 (ATCC 53973) is a derivative of the Connaught vaccine strain 10536 in which the TOX operon has been deleted and replaced by a cassette containing the *E. coli* S12 and tetracycline resistance genes (Zealey et al., Bio/Technology 8, 1025 [1990]; EPO 322,115, U.S. Pat. No. 5,085,862). Through homologous recombination, the S12/Tet$^R$ gene cassette is replaced by tandem copies of TOX to generate a strain (1190-74) which produces approximately two to three times the amount of PT produced by the wild-type strain. Similarly, tandem TOX* operons mutated to engineer a genetically detoxified PT analogue having the mutations Arg9→Lys9 and Gly129→Glu129 in the S1 subunit (Loosmore et al., Infect. Immun. 58, 3653 [1990]) have been introduced into strain 29-8 to generate strain 191- 134 (ATCC 55205).

Strain 390-101 (ATCC 55157) is a derivative of the Connaught vaccine strain 10536 in which the FHA gene locus has been replaced by the S12/Tet$^R$ gene cassette. An additional TOX operon has been inserted at the FHA locus of this strain to generate strain 590-208, which produces approximately twice as much PT as strain 10536, but no FHA.

Strain 989-56 (ATCC 53975) is a derivative of strain 10536 which expresses the PT analogue with Lys9-Gly129 mutations in S1 and is described in copending U.S. patent application Ser. No. 589,423 filed Sep. 18, 1990, assigned to the assignee hereof, the disclosure of which is incorporated herein by reference. Replacement of its FHA gene by the S12/Tet$^R$ gene cassette led to the TOX*/FHA$^-$ strain 490-324. Two additional tandem TOX* operons have been introduced at the FHA locus to generate a strain with three copies of TOX*, strain 890-393 (ATCC 55206), which expresses approximately three times the amount of PT analogue.

Using the same techniques, the PRN gene was deleted from strain 10536 to give strain 1090-108-3 (ATCC 55156). The PRN locus can similarly be used to introduce multiple copies of PRN or hybrid operons. The engineering of hybrid operons is described in our published European patent application EPO 453,216 and corresponding U.S. patent application Ser. No. 687,231 filed Apr. 18, 1991, assigned to the assignee hereof and the disclosure of which is incorporated herein by reference. Briefly, a hybrid operon consists of a structural gene from Bordetella placed under the control of the promoter of another gene of the same family. Tandem copies of a hybrid gene consisting of the pertactin structural gene under the regulation of the FHA promoter, were introduced into the PRN locus to generate strain 1091-297 which expresses approximately 20 times the amount of pertactin as the wild-type 10536 strain.

We have demonstrated that strains of *B. pertussis* can be engineered to eliminate the production of specific antigens or to overproduce specific antigens as a result of an increase in gene copy number. The additional gene copies may be single or multiple copies placed at the natural or novel loci through homologous recombination. They may be native or mutated genes or novel hybrid genes. They also may be heterologous genes from other bacterial species. The use of gene deletion and subsequent insertion of single or multiple natural or novel genes has great potential for optimizing the production of antigens for new vaccine formulations. Undesirable genes may be removed, expression of antigens produced in limiting amounts may be enhanced, and purification procedures simplified by the use of the techniques described herein. The requirement for certain growth supplements may be eliminated as a result of the efficient expression of selected antigens.

EXAMPLES

Methods of molecular genetics, protein biochemistry, and fermentation and hybridoma technology used but not explicitly described in this disclosure and these Examples are amply described in the scientific literature and are well within the ability of those skilled in the art.

Example 1

This Example illustrates the generic techniques used for vector and strain constructions and their molecular characterizations.

DNA manipulations, Southern blot analysis, and nick-translation of probes were according to Sambrook et al. (Molecular cloning: a laboratory manual/second edition. Cold Spring Harbor Laboratory, Cold Spring Harbor, N.Y. [1989]). Restriction enzymes were used according to the manufacturers' specifications. Genes were cloned from a *B. pertussis* 10536 genomic library prepared in lambda Charon 35 (described in EPO 322,115, U.S. Pat. No. 5,085,862). Plasmid DNA for electroporetic transformation was prepared according to Ish-Horowicz and Burke (Nucl. Acids Res. 9, 2989 [1988]). Chromosomal DNA for Southern blots was prepared according to Yacoob and Zealey (Nucl. Acids Res. 16, 1639 [1988]).

Example 2

This Example describes the procedure for gene replacement in the *Bordetella pertussis* chromosome by unmarked allelic exchange.

The same principle applies to both specific gene deletion and insertion of additional genes. Specific gene deletion, in fact, involves the insertion of a marker cassette. *B. pertussis* was transformed by electroporation as described in Zealey et al., Bio/Technology 8, 1025 [1990]. Briefly, cells were grown in 1 liter of Stainer Scholte medium supplemented with heptakis(2,6-0-dimethyl)β-cyclodextrin (Imaizumi et al., Infect. Immun. 41, 1138 [1983]) to a density of about $5 \times 10^9$ cells/ml and harvested by centrifugation (5000×g, 15 min., 4° C.). The cells were washed twice with 500 ml of distilled water and once in 50 ml of 10% glycerol, then resuspended in 10 ml of 10% glycerol, aliquotted, and frozen at −70° C. For transformation, 200 ul of cells were combined with 10–50 ug of linearized DNA or 5 ug of circular plasmid DNA and incubated on ice for 10 min. The mixture was subjected to a 650 V exponential decay pulse across a 0.8 mm electrode gap using a BTX Transfector 100 equipped with a Power Plus unit (Biotechnologies and Experimental Research, San Diego Calif.). One ml of medium was added and the cells incubated with shaking at 36° C. For integration of TOX alleles at the TOX locus of a TOX− strain, cells were transformed with linearized DNA. After transformation and one hour of non-selective growth, 50 ug/ml of ampicillin was added to the culture, and the incubation continued for 15–24 h at 36° C. One ml samples were plated onto Bordet-Gengou medium containing 100 ug/ml streptomycin and transformants appeared after 3–5 days of incubation at 36° C.

To increase the success of correct integration at the FHA locus, FHA deleted *B. pertussis* strains were transformed in two stages. Electroporation of circular plasmid DNA was performed and integration of the entire plasmid was selected for by resistance to ampicillin (50 μg/ml) Ap$^R$, Tet$^R$, Str$^S$ transformants were obtained at a frequency of about 500 per ug of DNA, and were presumably due to the integration of the entire plasmid at either the TOX or FHA locus. When these primary transformants were streaked onto medium containing streptomycin, Str$^R$ colonies were obtained in which the S12/Tet$^R$ gene cassette was replaced by the TOX operon by intramolecular recombination.

Example 3

This Example illustrates the growth of strains and antigen characterization.

Strains were routinely grown in 10 liter ChemAp bioreactors in modified Stainer-Scholte medium containing 0.2% heptakis (2,6-O-dimethyl)β-cyclodextrin (Imaizumi et al, Infect. Immun. 41., 1138 [1983]) with controls for temperature, pH, and dissolved oxygen, or in 10 ml culture. Culture supernatants were tested for antigen production in antigen-specific ELISAs using monospecific polyclonal and/or monoclonal antibodies. PT was measured in a fetuin-capture ELISA as described in Loosmore et al. (Infect. Immun. 58, 3653 [1990]). FHA was captured by a mouse monoclonal anti-FHA antibody purified from ascites fluid and the second antibody was a polyclonal rabbit IgG anti-FHA conjugated to horseradish peroxidase. Purified antigens were used as standards.

Pertussis toxin was purified as described in EPO 322,115, U.S. Pat. No. 5,085,862 and U.S. Pat. No. 4,997,915 assigned to the assignee hereof and the disclosure of which is incorporated herein by reference. A comparative analysis of PT analogues produced from strain 989-56 and the triple copy TOX* strain 890-393, showed no difference in SDS-PAGE patterns and HPLC profiles, as shown in FIGS. 4A, 4B and 4C. Table 2 below summarizes the biological properties of native PT and PT analogue produced by wild-type and engineered strains. Results indicate that PT secreted by single-copy or multiple-copy strains are functionally equivalent.

Example 4

This Example illustrates the generation of the FHA-deleted strain 390-101.

The FHA operon was originally cloned in two steps. An internal 4.5 kb BamH I/BamH I fragment of the FHA B structural gene was cloned from a pEV-based expression library (R. Crowl et al., Gene 38, 31 [1985]) using a polyclonal anti-FHA antibody as probe. This fragment then was nick-translated and used to probe a Charon phage pertussis genomic library to clone the whole operon.

An 11 kb internal EcoR I/EcoR I fragment of the FHA structural gene was deleted and replaced by the S12/Tet$^R$ gene cassette to generate plasmid pGZ71, which therefore has 2.5 kb of Bgl II/EcoR I 5'-FHA flanking sequence and 1.7 kb of EcoR I/Cla I 3'-FHA flanking sequence (FIG. 1A).

FIG. 1B demonstrates the construction of plasmid pGZ71. Briefly, plasmid S-2224-1 contains a chromosomal clone representing the 3'-Bgl II/EcoR I portion of the FHA operon and the S-3595-9-1 plasmid a chromosomal clone of the 5'-EcoR I/Bgl II portion of the FHA operon. If the two clones are joined at the Bgl II site, the entire FHA structural gene is reconstituted. Plasmid S-2224-1 was cleaved with Bgl II and EcoR I to give a pBR322-based vector fragment containing 1.7 kb of FHA 3'-flanking region (3' FHA). Plasmid S-3595-9-1 was digested with Bgl II and EcoR I and the 2.5 kb fragment containing the FHA 5'-flanking sequence (5'FHA) was ligated with the vector piece from S-2224-1 to yield plasmid S-3616-2. Plasmid pGZ62 contains the S12/Tet$^R$ gene cassette in a pBR322-based plasmid and is described in detail in EPO 322,115, U.S. Pat. No. 5,085,862. Plasmid S-3616-2 was digested with EcoR I, filled in using Klenow polymerase, and dephosphorylated with calf alkaline phosphatase (CAP). pGZ62 was digested with EcoR I and Bal I, and filled in. The S-3616-2 vector fragment and pGZ62 insert fragment were ligated to give pGZ71. The filled in EcoR I and Bal I sites regenerate the EcoR I site.

Electroporetic transformation of a spontaneous streptomycin resistant derivative of *B. pertussis* strain 10536, i.e. *B. pertussis* strain str29 (ATCC 53972), by linearized pGZ71 led to the deletion of the FHA structural gene by allelic exchange and yielded the FHA− strain 390-101 (ATCC 55157). The deletion of the FHA gene was confirmed by Southern blot analysis and FHA-specific ELISA. Similarly, plasmid pGZ71 was used to delete the FHA gene from *B. pertussis* strain 989-56 containing a TOX* operon to generate *B. pertussis* strain 490-324.

Example 5

This Example describes the generation of the FHA-deleted strain 590-208 which contains two copies of TOX at different genetic loci.

A pBR322-based plasmid (S-3741-2) was constructed which contains a single copy of the 4.7 kb EcoR I/EcoR I TOX operon between the FHA flanking region as described in Example 4. FIG. 1B describes the construction of plasmid S-3741-2. Briefly, S-3616-2 was digested with EcoR I, which opened the plasmid between the FHA flanking regions, and dephosphorylated with CAP. Plasmid J-169-1 is a pUC-based clone of TOX which was digested with EcoR I to produce an EcoR I/EcoR I TOX fragment. Upon ligation, S-3741-2 was generated which contains a single copy of the wild-type TOX operon between the FHA flanking regions.

Introduction of S-3741-2 by electroporation into the FHA-deleted strain 390-101, generated a strain having two non-tandem copies of TOX, strain 590-208. Southern blot analysis of strain 590-208 genomic DNA showed the correct placement of the additional TOX operon at the FHA locus.

When grown in liquid culture, the yield of PT was twice that obtained from the native strain as shown in Tables 1A and 1B below, but there was, as expected, no FHA production. Plasmid S-3741-2 has been deposited with the ATCC (accession number 75031).

Example 6

This Example illustrates the generation of the FHA-deleted strain 890-393, which contains three copies of the TOX* operon.

Figure 1C:
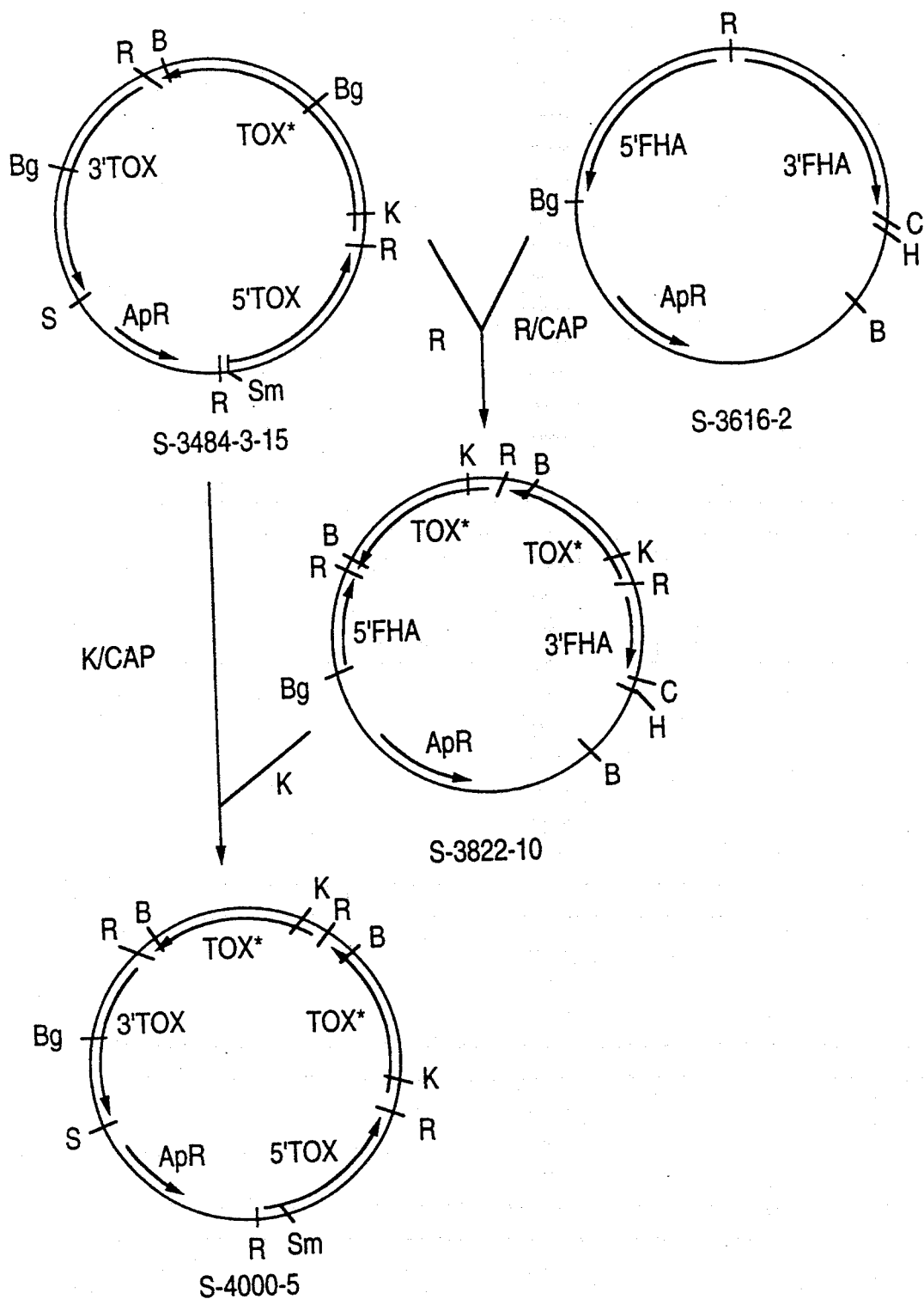

A pBR322-based plasmid (S-3822-10) was constructed to harbour two tandem copies of the 4.7 kb EcoR I/EcoR I TOX* operon between the FHA flanking regions described in Example 4 (FIG. 1A). The construction of S-3822-10 is illustrated in FIG. 1C. Briefly, plasmid S-3484-3-15 is a pUC-based vector containing the TOX 5'- and 3'-flanking sequences surrounding a mutated TOX operon (TOX*). The TOX* operon contains the mutations designed to produce a detoxified PT analogue with the Lys9Gly129 substitutions in its S1 subunit (Loosmore et al., Infect. Immun. 58, 3653 [1990]). S-3616-2 was digested with EcoR I and dephosphorylated. S-3484-3-15 was digested with EcoR I and the TOX* fragment cleaved out. A 5 molar excess of the EcoR I-EcoR I TOX* insert was used in the ligation reaction to force in tandem gene copies and plasmid S-3822-10 was obtained which contains two adjacent copies of TOX* between the FHA gene flanking regions, as confirmed by restriction enzyme analysis.

Figures 2A, 2B:
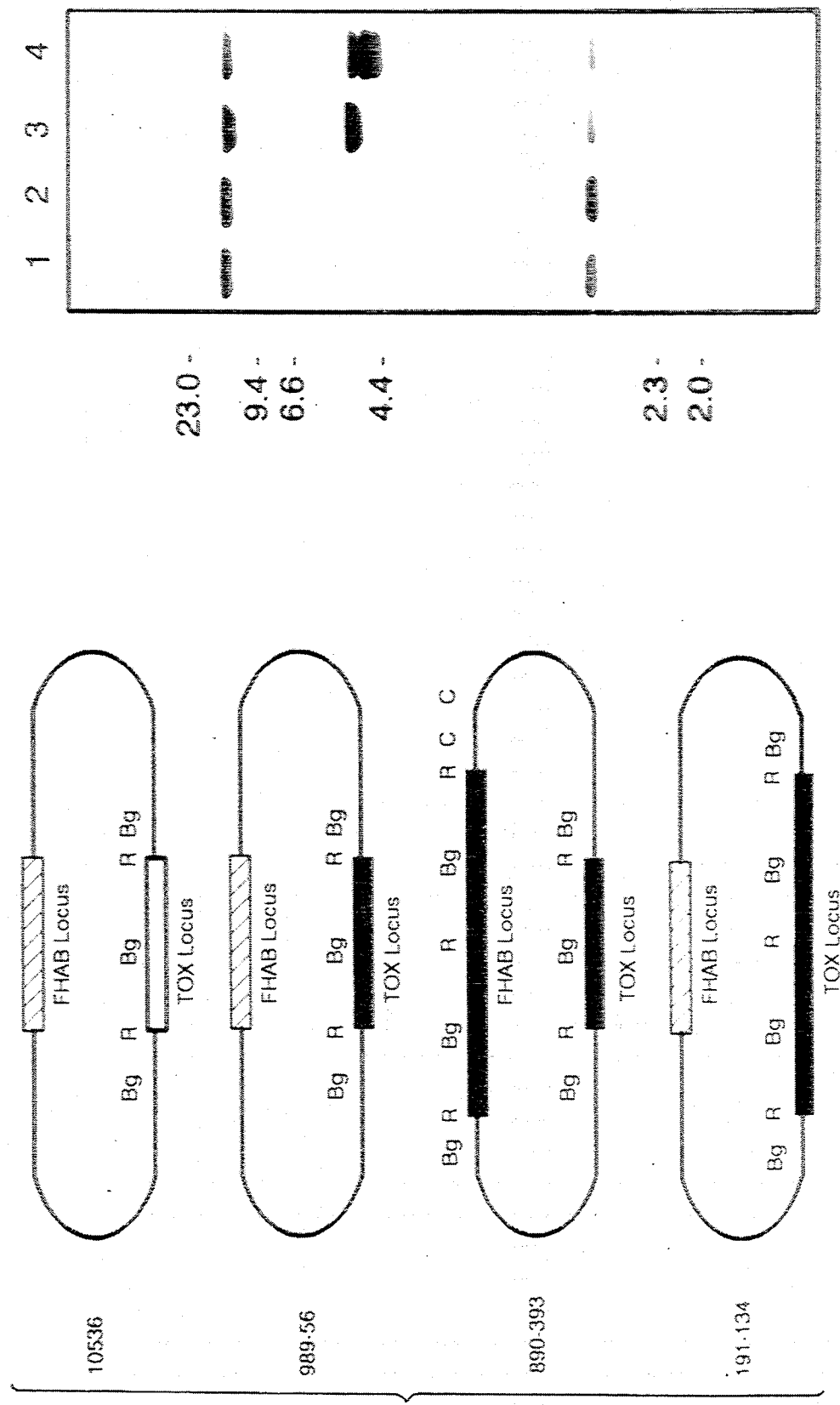
FIG. 2A shows a schematic representation of the genes present at the TOX and FHA loci and FIG. 2B shows the Southern blot analysis for B. pertussis strains 10536, 989-56, 191-134, and 890-393. Lane 1, strain 10536, the parental wild-type (wt) strain; lane 2, strain 989-56 containing one copy of TOX*; lane 3, strain 191-134 containing tandem copies of TOX* at the TOX locus; and lane 4, strain 890-393 containing three copies of TOX* one at the TOX locus and tandem copies at the FHA locus. DNA was digested with Bgl II and Cla I and probed with a TOX-specific DNA fragment representing the entire TOX operon. Integration of additional copies of the TOX operon is shown by the appearance of new TOX-specific hybridization fragments superimposed upon the wild-type pattern. Restriction sites are Bg, Bgl II; C, Cla I; and R, EcoR I.
Figure 3:
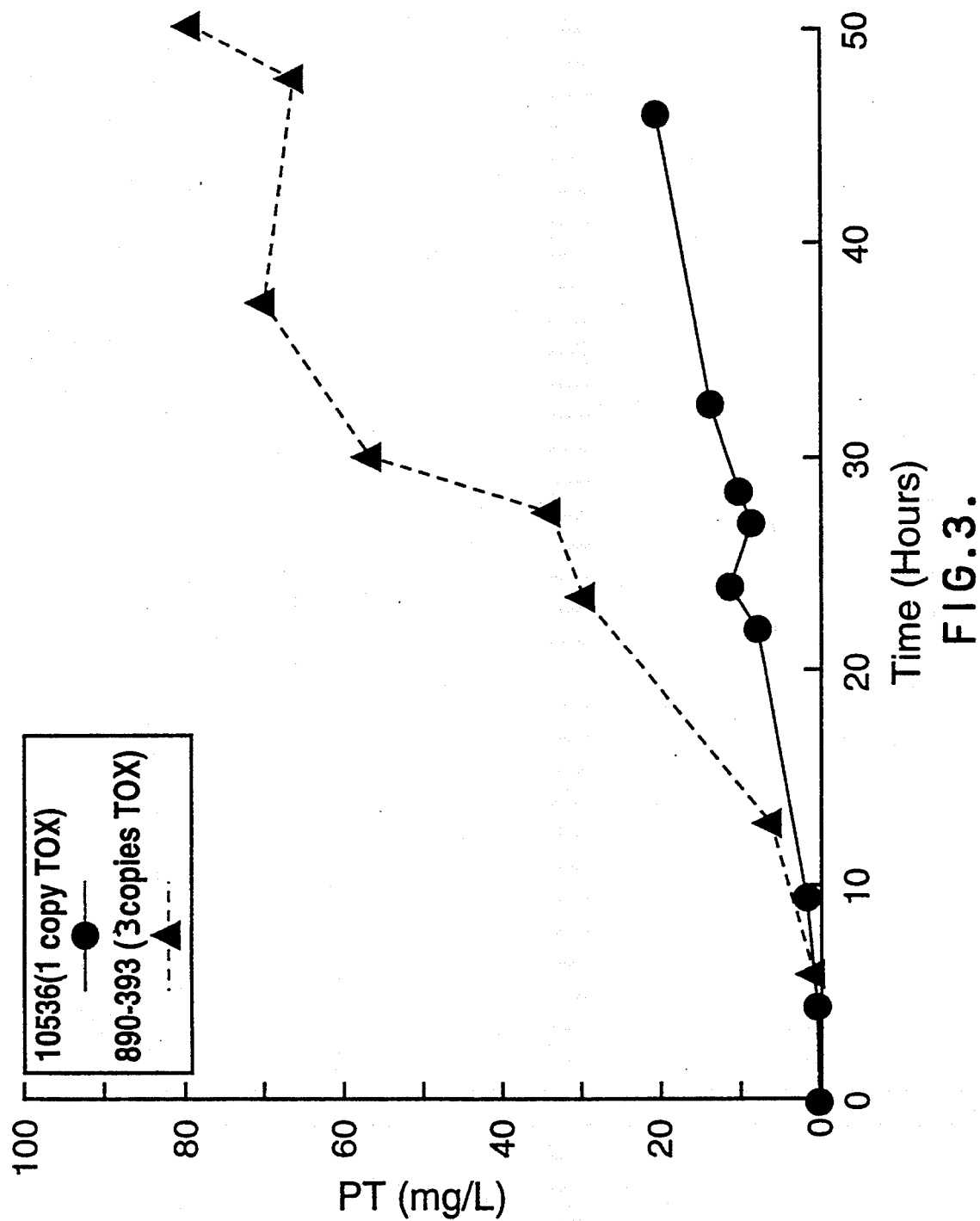
FIG. 3 shows the kinetics of PT or PT analogue expression for strains 10536 (wt), and 890-393 (3 TOX*) when grown in 10 liter bioreactors.

Strain 989-56 (ATCC 53975) is the derivative of the 10536 wild-type strain which expresses the Lys9Gly129 PT analogue (FIG. 2). pGZ71 was used to delete the FHA structural gene from 989-56 to give strain 490-324, which is TOX* FHA−. Introduction of S-3822-10 into 490-324 led to the generation of strain 890-393 which contains three copies of the TOX* operon, two at the FHA locus and one at the original TOX locus (FIG. 2A). When grown in liquid culture, as described in Example 3, the expression of PT analogue was found to be 3 to 4 times that obtained from strain 10536, as shown in Tables 1A and 1B below. FIG. 3 demonstrates the kinetics of PT analogue expression from *B. pertussis* strain 890-393.

FIG. 2B shows the Southern blot analysis of genomic DNA from strain 890-393. Chromosomal DNA was isolated, restricted simultaneously with Bgl II and Cla I and probed with a nick-translated TOX-specific probe. The hybridization pattern of restricted genomic DNA from *B. pertussis* 890-393 (lane 4) was compared with that of DNA obtained from strain 10536 (lane 1) and strain 989-56 (lane 2), and revealed the presence of the 3.3 and 13 kb TOX-specific fragments characteristic of the native TOX operon. For strain 890-393, however, the predicted additional TOX-specific fragments of 5.3, 5.0, and 3.7 kb were observed. The hybridization pattern indicated that this strain had one TOX* operon at the TOX locus and two more copies in tandem at the FHA locus. Strain 890-393 has been deposited with the ATCC (accession number 55206).

Example 7

This Example describes the generation and characterization of strain 191-134 which contains two tandem copies of TOX* at the TOX locus.

A pUC-based plasmid (S-4000-5) was constructed which contains two tandem copies of the TOX* operon, between the 5' and 3' TOX flanking regions. The 4.7 kb EcoR I/EcoR I TOX* fragment is defined as the operon and the 2.9 kb Sma I/EcoR I 5'-flanking and 4 kb EcoR I/Sal I 3'-flanking regions of the native TOX operon were used to direct the tandem genes to the TOX locus (see FIG. 1A). The TOX flanking regions have been extensively described in EPO 322,115, U.S. Pat. No. 5,085,862.

FIG. 1C illustrates the construction of plasmid S-4000-5. Briefly, the pUC-based plasmid S-3484-3-15, which contains the TOX* operon between the TOX flanking regions, was linearized with Kpn I and dephosphorylated. Plasmid S-3822-10 which contains tandem TOX* operons between the FHA flanking regions, was restricted with Kpn I and the 4.6 kb Kpn I/Kpn I fragment removed. Upon ligation of these pieces, plasmid S-4000-5 containing two tandem copies of TOX* between the TOX flanking regions was generated.

S-4000-5 was linearized with Hind III and strain 29-8 was transformed by electroporation to produce strain 191-134. Southern blot analysis of 191-134 genomic DNA showed the correct in situ placement of the tandem TOX* operons at the TOX locus, as shown in FIG. 2, lane 3. Chromosomal DNA was obtained from strain 191-134 and digested simultaneously with Bgl II and Cla I. When hybridized with a TOX-specific probe, the 13 and 3.3 kb bands which indicate the presence of a single copy of TOX at the TOX locus were observed, but an additional 5.0 kb band also was detected. This pattern indicates the presence of two tandem copies of TOX* at the TOX locus. When grown in liquid culture, the kinetics of PT analogue production by strain 191-134 are similar to those of the native strain but 2 to 3 times more PT analogue was produced as shown in Tables 1A and 1B below. Strain 191-134 has been deposited with the ATCC (accession number 55205).

Example 8

This Example illustrates the engineering and characterization of strain 1190-74 which contains two tandem copies of the wild-type TOX operon integrated at the TOX locus.

A pUC-based plasmid (S-3980-9) was constructed which is similar to S-4000-5, which contains two tandem copies of TOX* (Example 7), except that the TOX operon is wild-type. S-3980-9 was linearized with Hind III and introduced into the TOX deleted strain 29-8 by electroporetic transformation to generate strain 1190-74. Southern blot analysis of 1190-74 genomic DNA showed correct in situ placement of the tandem operons.

When grown in liquid culture, the kinetics of PT production from strain 1190-74 was similar to that obtained for the native strain but the yield of PT was 2 to 3 times higher, as shown in Tables 1A and 1B below. Plasmid S-3980-9 has been deposited with the ATCC (accession number 75033).

Example 9

This Example illustrates the effect of PT overproduction on the requirement for cyclodextrin in the medium.

Figure 5A:
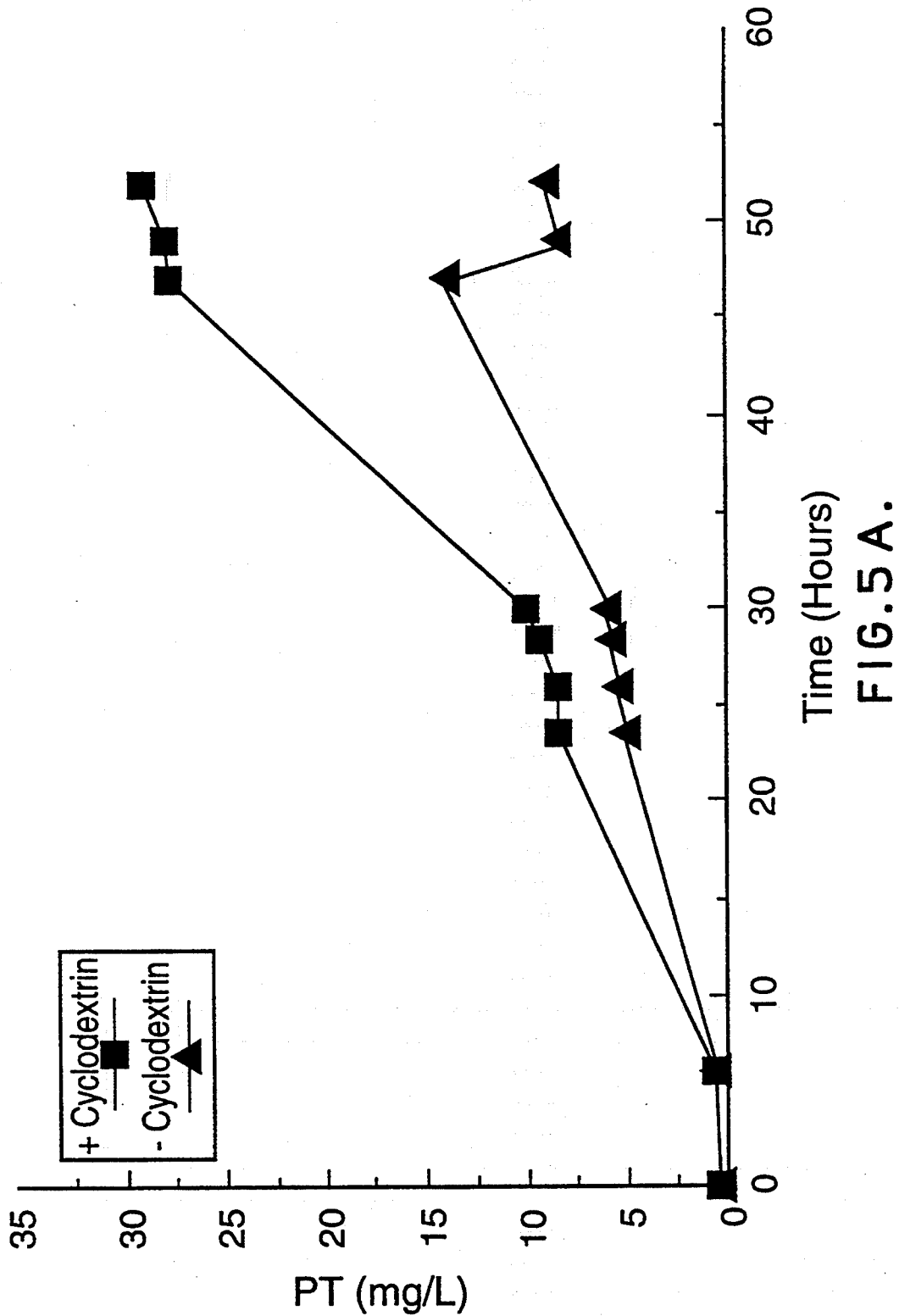
FIGS. 5A-5B
Figure 5B:
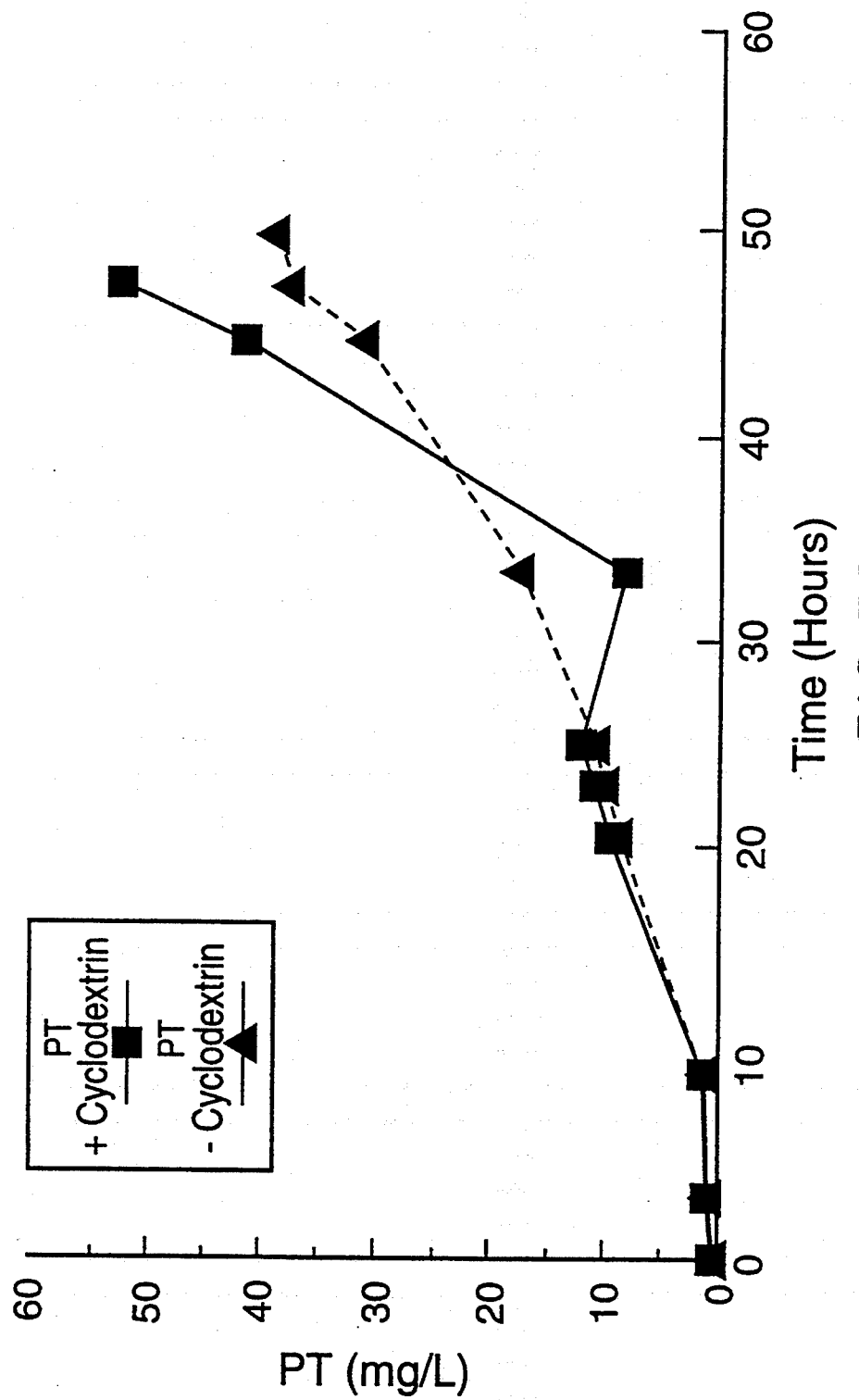

To optimize the expression of PT from a native strain, the medium is typically supplemented with a dextrin derivative, such as 0.2% (heptakis(2,6-O-dimethyl)β-cyclodextrin (Imaizumi et al., Infect. Immun. 41, 1138 [1983]). FIG. 5A demonstrates that the addition of cyclodextrin significantly enhances the concentration of PT in the fermentation broth of the wild-type strain 10536. Strain 1190-74 contains two tandem copies of the wild-type TOX operon. When grown in the absence of 0.2% heptakis(2,6-O-dimethyl)β-cyclodextrin, there is a negligible effect on the expression of PT, as illustrated in FIG. 5B. Similar results were observed for the PT analogue-producing strains. In addition, the overproduction of PT or PT analogue did not affect the expression of other antigens, such as FHA, agglutinogens, or pertactin.

Example 10

This Example illustrates the generation of the PRN deleted strain 1090-108-3.

Figure 1D:
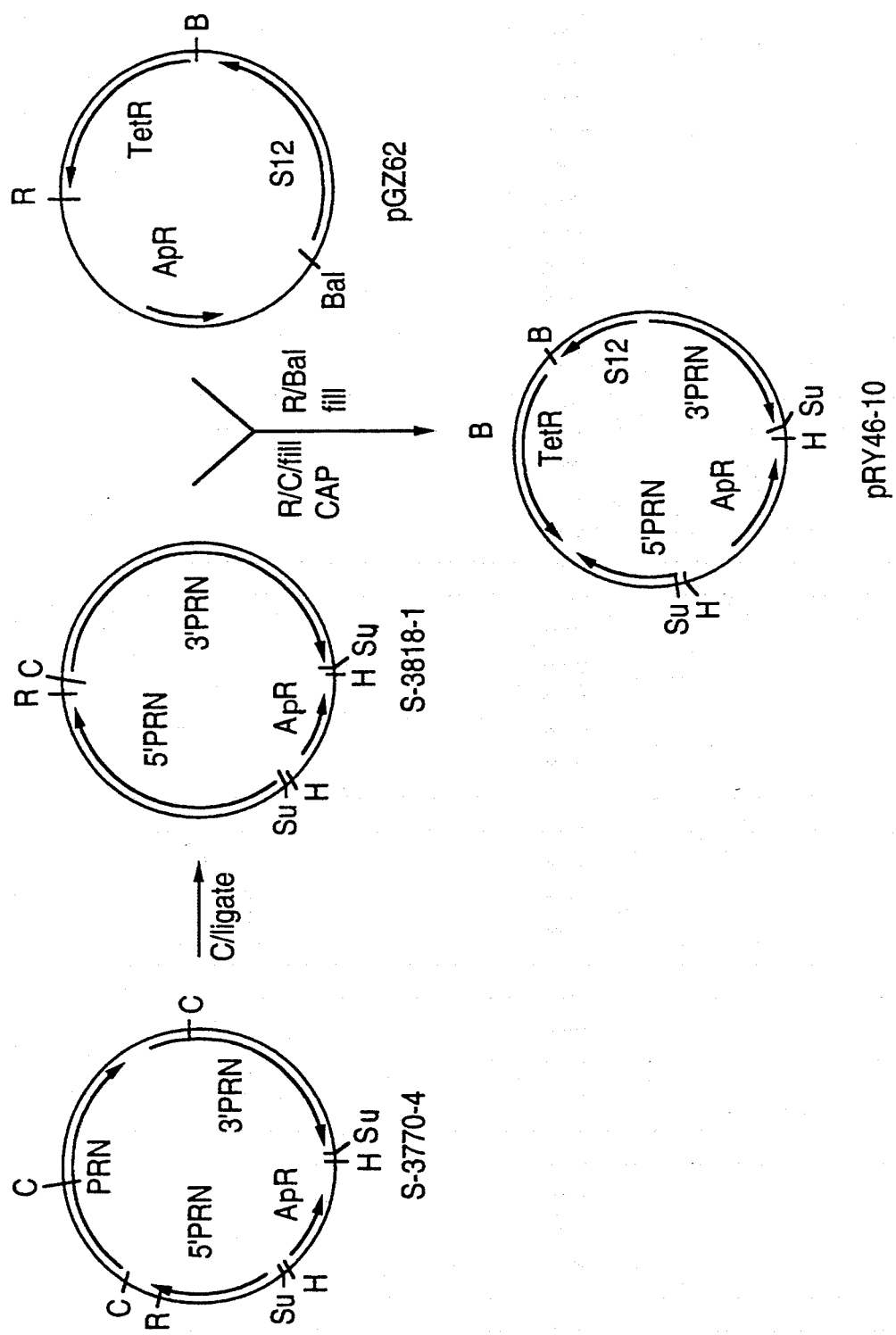

The PRN gene region was cloned as an 11.3 kb fragment from a Charon phage pertussis library using specific oligonucleotide probes. The oligonucleotide sequences were AATGAACATGTCTCTGTCACG-CATTGTCAA (SEQ. ID: No. 1) and TTCCACGCGGGCTACCGGTACAGCTGGTAA (SEQ. ID: No. 2) and represented sequence from base 144 to base 173 and base 2848 to base 2877 of the published PRN sequence, respectively (Charles et al., Proc. Natl. Acad. Sci. 86, 3554 [1989]). Plasmids S-3596-1-1 and S-3770-4 are chromosomal subclones of the entire pertactin gene region, PRN (FIG. 1D). Digestion of S-3770-4 with Cla I deleted the internal 7 kb Cla I/Cla I fragment of the coding sequence and re-ligation gave plasmid S-3818-1. This pUC-based plasmid contains the 1.6 kb of Sau3A I/Cla I 5'-flanking sequence and 3.5 kb of Sau3A I/Cla I 3'-flanking sequence from PRN. S-3818-1 was digested with EcoR I and Cla I, filled in using Klenow polymerase, and dephosphorylated. Plasmid pGZ62 was digested with EcoR I and Bal I to remove the S12/Tet$^R$ gene cassette, which then was filled in. Ligation of the fragments gave pRY46-10 which contains the selection cassette between the PRN flanking regions (FIG. 1A).

When linearized PRY46-10 was introduced into strain str29 (wild type, ATCC no. 53972), strain 1090-108-3 was generated in which the PRN gene region has been deleted. Southern blot analysis confirmed the replacement of the PRN gene sequences by the S12/Tet$^R$ gene cassette. Pertactin-specific ELISAs demonstrated that strain 1090-108-3 did not produce this antigen. Strain 1090-108-3 has been deposited with the ATCC (accession number 55156).

Example 11

This Example illustrates the generation of B. pertussis strain 1091-297 which contains two tandem copies of the FHApPRN alleles integrated at the PRN locus.

Figure 1E:
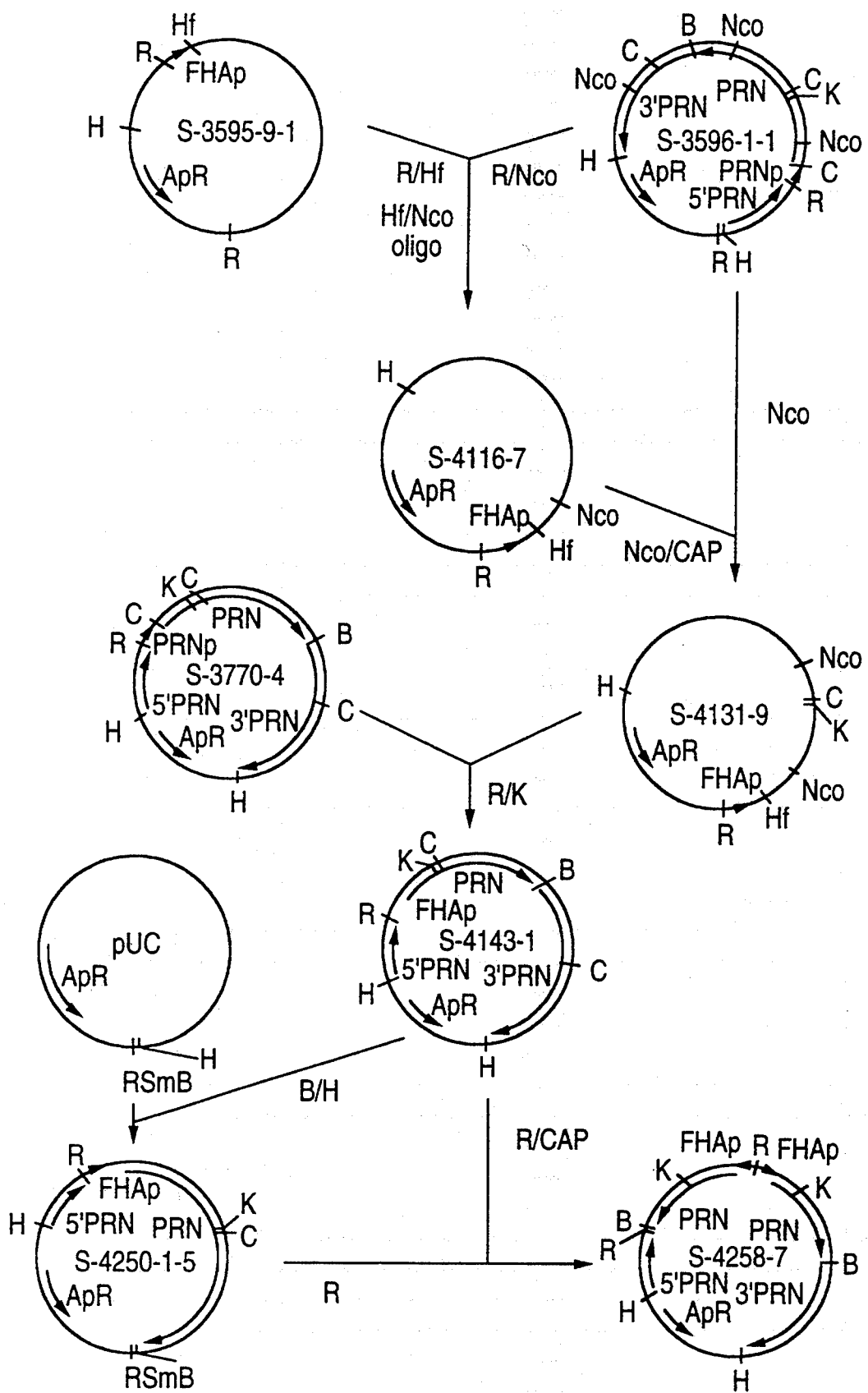

A pUC-based plasmid (S-4258-7) was constructed that contained two copies of the FHApPRN hybrid gene sandwiched between the 5'- and 3'-flanking regions of PRN. FIG. 1E illustrates the construction of plasmid S-4258-7. The construction of hybrid genes is described in detail in EPO 453,216, U.S. Ser. No. 687,231. Briefly, plasmid S-3595-9-1 is a chromosomal subclone of the FHA 5'-flanking region and 5'-portion of FHAB including the FHA promoter region. Plasmid S-3596-1-1 is a chromosomal subclone of the PRN gene locus including the flanking regions. Plasmid S-3595-9-1 was digested with EcoR I and Hinf I to generate a 240 bp EcoR I/Hinf I fragment containing most of the FHA promoter. Plasmid S-3596-1-1 was digested with EcoR I and Nco I to generate a 4 kb piece containing pUC with part of the 3'-flanking region of PRN. A 93 bp Hinf I/Nco I oligonucleotide was used to join the fragments and generate plasmid S-4116-7, which therefore contains the whole FHA promoter and part of the PRN signal sequence up to the Nco I site. Plasmid S-3596-1-1 was digested with Nco I to generate a 2.2 kb fragment containing most of the PRN structural gene. Plasmid S-4116-7 was linearized with Nco I and dephosphorylated with calf alkaline phosphatase. Ligation of the structural gene fragment behind the FHA promoter gave plasmid S-4131-9. Plasmid S-3770-4 is a chromosomal subclone of the PRN gene locus including flanking regions. Digestion of S-3770-4 with Kpn I and EcoR I removes the natural PRN promoter and part of the structural gene. Plasmid S-4131-9 was digested with EcoR I and Kpn I and the fragment containing the FHA promoter and 5'-half of the PRN structural gene, was ligated into the S-3770-4 vector fragment to generate plasmid S-4143-1 which thus has one copy of the FHApPRN hybrid gene. S-4143-1 was digested with BamH I and Hind III and the 5.6 kb fragment containing the 5'-PRN and FHApPRN hybrid gene was inserted into pUC digested with BamH I and Hind III to generate plasmid S-4250-1-5 which now has the hybrid gene between two EcoR I sites. Plasmid S-4143-1 was linearized with EcoR I and dephosphorylated. S-4250-1 was digested with EcoR I to release the hybrid gene which was ligated into the EcoR I site of S-4143-1 to produce plasmid S-4258-7 which has two tandem copies of the hybrid gene in opposite orientations.

Plasmid S-4258-7 was used to transform the PRN deleted strain 1090-108-3 in two stages. Electroporation of circular plasmid DNA was performed and integration of the entire plasmid selected for by resistance to ampicillin and tetracycline. When these primary transformants were streaked onto medium containing streptomycin, Str$^R$ colonies were obtained in which the S12/Tet$^R$ gene cassette was replaced by the FHApPRN hybrid genes by intramolecular recombination. B. pertussis strain 1091-297 (ATCC 55,462) containing two tandem copies of the FHApPRN hybrid genes was generated in this fashion. Southern blot analysis showed the correct placement of the two hybrid genes at the PRN locus as demonstrated in FIG. 6B. When grown in liquid culture, the kinetics of pertactin production were similar to the wild-type strain but the total yield of protein was approximately 20-fold higher (Table 3).

Example 12

This Example describes the construction of B. pertussis strains which overproduce both pertussis toxin and pertactin.

Figure 7B:
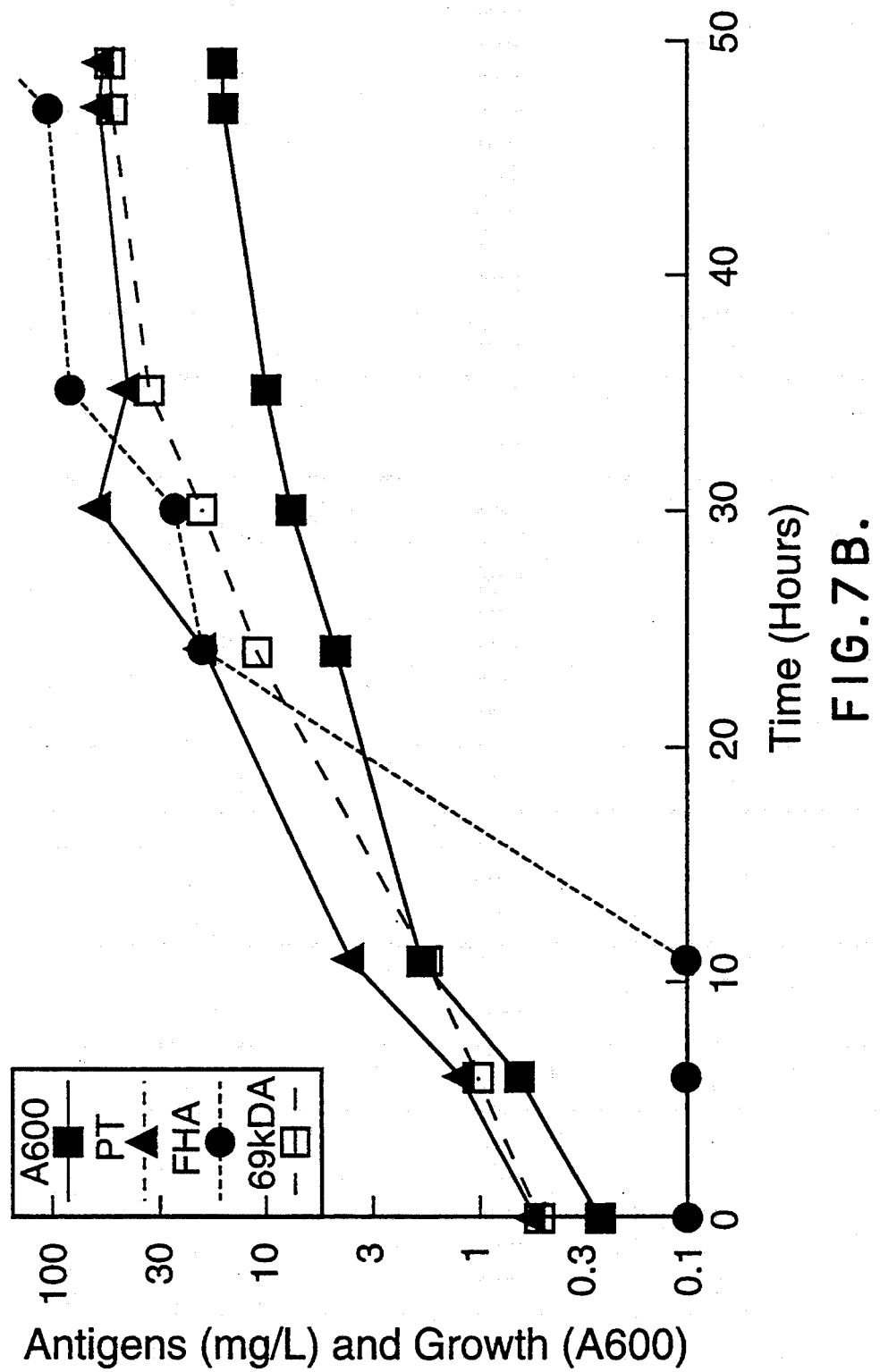

In the EPO 453,216 and U.S. Ser. No. 687,231, the inventors described the generation of hybrid genes as a means to improve antigen expression. In Example 11 above, the construction of plasmid S-4143-1, which contains an FHApPRN hybrid gene, is described. Plasmid S-4143-1 was used to transform the PRN—deleted B. pertussis strain 1090-108-3 (ATCC 55156) and produce strain 591-473 (ATCC 55,321), which contains a single copy of the hybrid FHApPRN gene at the PRN locus. The TOX operon of B. pertussis 591-473 was replaced by the selectable S12/Tet$^R$ cassette, as described in Example 4 above, to generate B. pertussis strain 891-98. Two tandem copies of wild-type TOX or mutant TOX* were integrated at the TOX locus by transformation with plasmids S-3980-9 or S-4000-5, respectively, as described in Examples 7 and 8 above. This action generated B. pertussis strain 1091-107 (ATCC 55,313) which overexpresses wild-type PT and pertactin and strain 1091-359 (ATCC 55,312) which overexpresses the Lys9Gly129 PT analogue and pertactin. FIGS. 7A and 7B illustrate the levels of antigen production from strains 1091-107 and 1091-359 when grown in 10 liter fermentors.

Table 1 provides details of the production of PT and FHA from certain strains of Bordetella pertussis wherein modification to the TOX operon has been effected. The effect of the presence of multiple gene copies on antigen production can be seen from the data presented (see Examples 7 and 8).

Table 2 provides details of the biological characterization of certain strains of B. pertussis.

Table 3 provides details of the production of PT and FHA from certain strains of B. pertussis wherein modification to the PRN operon has been effected. The effect of the presence of multiple hybrid gene copies on antigen production can be seen from the data provided (see Example 11).

TABLE 1A

Production of pertussis toxin (PT) and filamentous haemagglutinin (FHA) by strains of Bordetella pertussis that contain multiple copies of the TOX operon. Strains contained either the wild-type TOX operon or the genetically detoxified Lys9 Gly129 allele located at either the TOX or FHA loci as indicated. They were grown in 10 ml shake-flasks and antigens in culture supernatants determined by antigen-specific ELISAs.

| Strain | Gene at TOX Locus | Gene at FHA Locus | Transformed Strain | Plasmid | Antigen Production ($\mu g/ml$)[a] PT | FHA |
|---|---|---|---|---|---|---|
| 10536 | TOX$^{wild-type}$ | FHA | | | 4.7 ± 0.6 | 58.7 ± 4.5 |
| 29-8 | Δ | FHA | | | 0 | 48.1 ± 3.4 |
| 390-101 | TOX$^{wild-type}$ | Δ | Str29 | pGZ71 | 4.1 ± 0.9 | 0 |
| 490-324 | TOX$^{Lys9Gly129}$ | Δ | 989-56 | pGZ71 | 3.9 ± 0.8 | 0 |
| 590-208 | TOX$^{wild-type}$ | TOX$^{wild-type}$ | 390-101 | S-3741-2 | 9.4 ± 0.8 | 0 |
| 1190-74 | 2TOX$^{wild-type}$ | FHA | 29-8 | S-3980-9 | 20.6 ± 1.5 | 54.2 ± 2.4 |
| 191-134 | 2TOX$^{Lys9Gly129}$ | FHA | 29-8 | S-4000-5 | 12.9 ± 1.0 | 49.3 ± 3.88 |
| 890-393 | TOX$^{Lys9Gly129}$ | 2TOX$^{Lys9Gly129}$ | 490-324 | S-3822-10 | 19.9 ± 1.2 | 0 |

[a]Expressed as mean ± standard errors at 95% confidence limits for at least four independent experiments.
Δ deleted gene.

TABLE 1B

Production of pertussis toxin (PT) and filamentous haemagglutinin (FHA) by strains of Bordetella pertussis that contain multiple copies of the TOX operon. Strains contained either the wild-type TOX operon or the genetically detoxified Lys9 Gly129 allele located at either the TOX or FHA loci as indicated. They were grown in 10 L bioreactors and antigens in culture supernatants determined by antigen-specific ELISAs.

| Strain | Gene at TOX Locus | Gene at FHA Locus | Transformed Strain | Plasmid | Antigen Production (mg/l) PT | FHA |
|---|---|---|---|---|---|---|
| 10536 | TOX$^{wild-type}$ | FHA | | | 20 | 90 |
| 989-56 | TOX$^{Lys9Gly129}$ | FHA | | | 20 | 80 |
| 590-208 | TOX$^{wild-type}$ | TOX$^{wild-type}$ | 390-101 | S-3741-2 | 40 | 0 |
| 1190-74 | 2TOX$^{wild-type}$ | FHA | 29-8 | S-3980-9 | 52 | 73 |
| 191-134 | 2TOX$^{Lys9Gly129}$ | FHA | 29-8 | S-4000-5 | 34 | 70 |
| 890-393 | TOX$^{Lys9Gly129}$ | 2TOX$^{Lys9Gly129}$ | 490-324 | S-3822-10 | 80 | 0 |

TABLE 2

Biological characterization of PT analogues obtained from Bordetella pertussis strains that over-produce pertussis toxin.

| Strain | Number of TOX Operons | PT Produced | Relative CHO Cell Clustering Activity (%) | Relative ADPR Activity (%) | Histamine Sensitization ($LD_{50}$ $\mu g$)[a] | Mouse Protection ($ED_{50}$ $\mu g$)[b] |
|---|---|---|---|---|---|---|
| 10536 | 1 | Wild-type | 100 | 100 | 0.05 | — |
| 989-56 | 1 | Lys$^9$Gly$^{129}$ | ≦0.0005 | <0.0001 | >50[c] | 4 |
| 890-393 | 3 | Lys$^9$Gly$^{129}$ | ≦0.0005 | <0.0001 | >50[c] | 4 |

[a]The $LD_{50}$ is the dose required to kill 50% of the mice following challenge with histamine acid phosphate (1 mg/10 g body weight).
[b]The $ED_{50}$ is the dose which protects 50% of the mice from an intracerebral challenge with B. pertussis 18323. This value cannot be determined for wild-type PT because of the toxicity of the molecule.
[c]No toxicity at the indicated dose.

TABLE 3

Production of pertussis toxin (PT), filamentous hemagglutinin (FHA) and pertactin, by Bordetella pertussis strains that contain one or two copies of the hybrid PRN allele at the PRN locus. The strains were grown in 10 ml shake-flasks and antigen levels in culture supernatants determined by antigen-specific ELISAs.

| Strain | Construction | Antigen Expression ($\mu g$ ml$^{-1}$)[a] PT | FHA | Pertactin |
|---|---|---|---|---|
| 10536 | wild-type | 5.9 ± 1.1 | 53.7 ± 10.1 | 8.9 ± 3.6 |
| 1090-108-3 | PRN Δ | 1.6 ± 0.9 | 31.9 ± 9.8 | 0 |
| 591-473 | FHApPRN | 4.7 ± 1.0 | 47.9 ± 9.4 | 73.6 ± 12.1 |

TABLE 3-continued

Production of pertussis toxin (PT), filamentous hemagglutinin (FHA) and pertactin, by *Bordetella pertussis* strains that contain one or two copies of the hybrid PRN allele at the PRN locus. The strains were grown in 10 ml shake-flasks and antigen levels in culture supernantants determined by antigen-specific ELISAs.

| Strain | Construction | Antigen Expression (μg ml$^{-1}$)[a] | | |
|---|---|---|---|---|
| | | PT | FHA | Pertactin |
| 1091-297 | 2xFHApPRN | 4.1 ± 2.0 | 86.7 ± 10.1 | 186.7 ± 15.8 |

[a]Concentrations are expressed as means ± standard errors at 95% confidence limits for at least five independent experiments.
Δ: deleted gene.

SUMMARY OF DISCLOSURE

In summary of this disclosure, the present invention provides novel strains of Bordetella which provide altered levels of gene expression, permitting enhanced antigen production and optimum purification. Modifications are possible within the scope of this invention.

What we claim is:

1. A genetically-modified Bordetella strain from which the FHA gene is absent from the genome of the strain and which contains an additional TOX gene in the genome of the strain.

2. The Bordetella strain of claim 1 which is identified as *Bordetella pertussis* strain 590-208 and which is derived from FHA− *Bordetella pertussis* strain 390-101 having ATCC accession number 55157 by chromosomal transformation employing plasmid S-3741-2 having ATCC accession number 75031.

3. A genetically-modified Bordetella strain from which the FHA gene is absent from the genome of the strain and which contains a genetically-detoxified mutant TOX* gene in the genome of the strain.

4. The Bordetella strain of claim 3 wherein said genetically-detoxified mutant TOX* gene encodes a pertussis toxin analog having mutations Glu129→Gly129 and Arg9→Lys9 in the S1 subunit of pertussis toxin.

5. The Bordetella strain of claim 3 which contains two tandemly-linked genetically-detoxified TOX* genes at the FHA locus and a single copy of the genetically-detoxified TOX* gene at the TOX locus and which is identified as *Bordetella pertussis* strain 890-393 having ATCC accession number 55206.

6. A genetically-modified Bordetella strain containing at least two tandem copies of a TOX gene or of a genetically-detoxified mutation thereof in the genome of the strain.

7. The Bordetella strain of claim 6 containing two TOX* genes encoding a pertussis toxin analog having the mutations Arg9→Lys9 and Glu129→Gly129 in the S1 subunit of pertussis toxin and which is identified as *Bordetella pertussis* strain 191-134 having ATCC accession number 55205.

8. The Bordetella strain of claim 6 containing two TOX (wild-type) genes and which is identified as *Bordetella pertussis* strain 1190-74 which is derived from the TOX− *Bordetella pertussis* strain 29-8 having ATCC accession number 53973 by chromosomal transformation employing plasmid S-3980-9 having ATCC accession number 75033.

9. A genetically-modified Bordetella strain containing, in the genome thereof, at least two copies (tandem or non-tandem) of a hybrid gene comprising the PRN structural gene under the regulation of the FHA promoter.

10. The Bordetella strain of claim 9 containing two tandem FHApPRN genes and identified as *Bordetella pertussis* strain 1091-297.

11. A genetically-detoxified Bordetella strain containing at least two copies of the TOX (wild-type) gene in the genome of the strain in combination with one or more hybrid genes in the genome of the strain, said hybrid gene comprising a Bordetella gene under the regulation of a promoter of another Bordetella gene.

12. The Bordetella strain of claim 11 which is identified as *Bordetella pertussis* strain 1091-107 having ATCC accession number 55313.

13. A genetically-modified Bordetella strain containing at least two copies (tandem or non-tandem) of a genetically-detoxified TOX* gene in the genome of the strain in combination with one or more hybrid genes in the genome of the strain, said hybrid gene comprising a Bordetella gene under the regulation of a promoter of another Bordetella gene.

14. The Bordetella strain of claim 13 wherein said TOX* gene encodes a pertussis toxin analogue having the mutations Arg9→Lys9 and Glu129→Gly129 in the S1 subunit of pertussis toxin.

15. The Bordetella strain of claim 14 which is identified as *Bordetella pertussis* strain 1091-359, having ATCC accession number 55312.

16. Plasmid S-3741-2 having ATCC accession number 75031.

17. Plasmid S-3980-9 having ATCC accession number 75033.

18. A vaccine against Bordetella infection comprising, as a single component or as one component of a multicomponent vaccine, a killed Bordetella strain of claims 1, 3, 6, 9, 11 or 13.

19. A process of producing an antigen, which comprises:
    culturing a genetically-modified Bordetella strain of claims 1, 3, 6, 9, 11 and 13 in a culture medium to effect expression of a protein encoded by genes present in said strain.

20. The process of claim 19 wherein said protein is extracted from said culture medium and detoxified for vaccine use.

* * * * *